United States Patent [19]

Landell

[11] 4,453,786
[45] Jun. 12, 1984

[54] MOUNTING ARRANGEMENT FOR TABLET-LIKE RUST INHIBITOR

[75] Inventor: Harper Landell, Downingtown, Pa.

[73] Assignee: Woodstream Corporation, Lititz, Pa.

[21] Appl. No.: 420,302

[22] Filed: Sep. 20, 1982

[51] Int. Cl.³ ............................................. A61L 9/00
[52] U.S. Cl. ..................................... 312/31.1; 312/31
[58] Field of Search ....................... 239/58, 59, 60, 55, 239/56; 206/213.1; 312/31, 31.1; 248/30

[56] References Cited

U.S. PATENT DOCUMENTS

| | | | |
|---|---|---|---|
| 2,419,299 | 4/1947 | Tanner | 312/31 |
| 2,508,773 | 5/1950 | Reichmuth | 312/31.1 X |
| 4,219,145 | 8/1980 | Jaeschke et al. | 239/60 X |
| 4,361,279 | 11/1982 | Beacham | 239/56 |

Primary Examiner—William E. Lyddane
Assistant Examiner—Joseph Falk
Attorney, Agent, or Firm—Holman & Stern

[57] ABSTRACT

A module for firmly retaining a tablet-like member to optimize air flow around the member includes a slotted front wall and a rear wall defining an enclosure therebetween. Two vanes projecting from one wall terminate in respective spaced parallel edges which urge the tablet-like member against the edge of a third vane projecting from the opposite wall when the tablet-like member is inserted into the enclosure from an open bottom end. The front wall and a portion of the rear wall are multiply slotted to facilitate air flow around the tablet. Centering members are provided to automatically transversely center the tablet with respect to the vanes when it is inserted into the enclosure. The rear wall of the module extends transversely to define shoulders which slidably engage opposing shoulders in a mounting support forward at the right angle junction of two walls in a container in which the module is disposed. A projection from one container wall urges the module rear wall forward to firmly engage the slidable shoulders. A snap-fit engagement is provided for the module in the mounting support.

11 Claims, 6 Drawing Figures

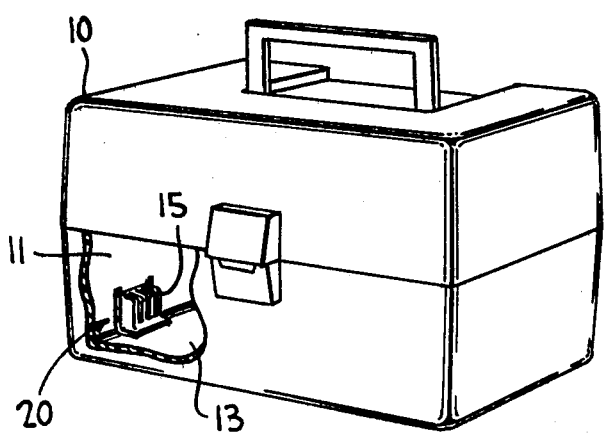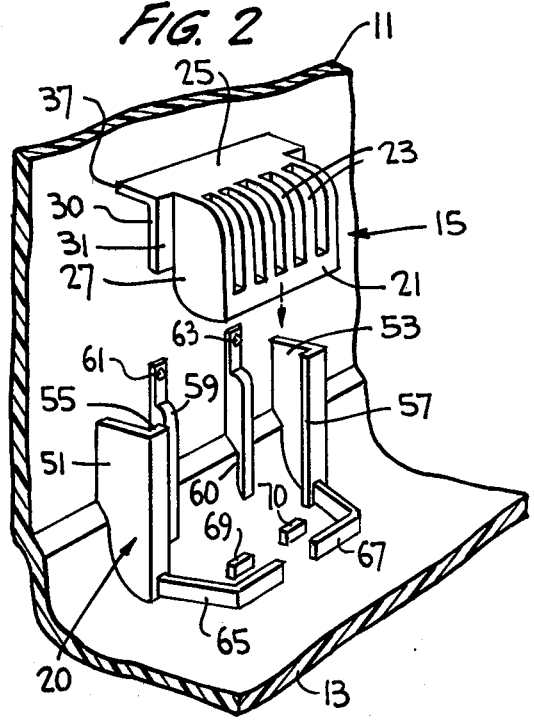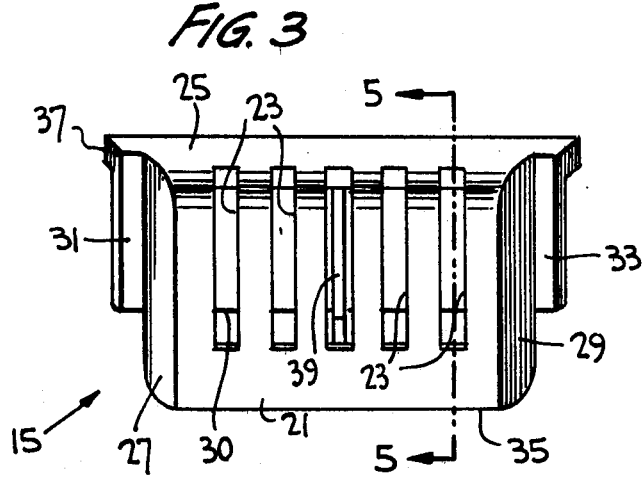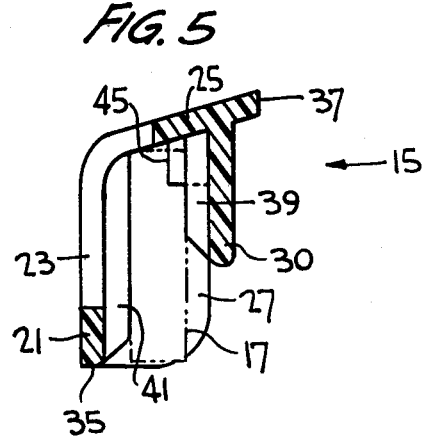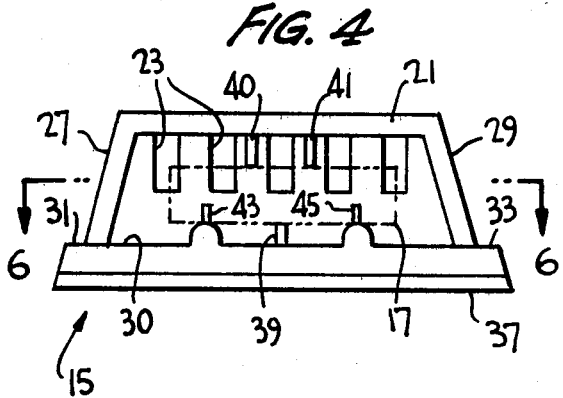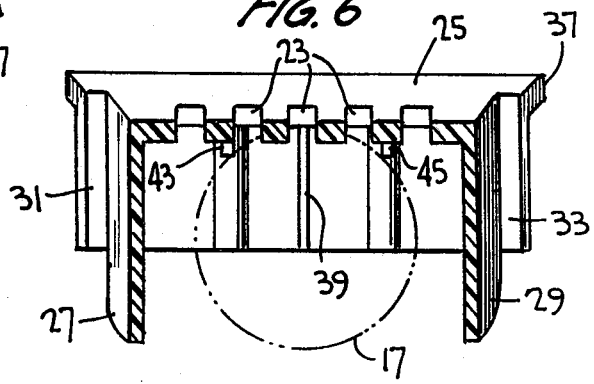

MOUNTING ARRANGEMENT FOR TABLET-LIKE RUST INHIBITOR

BACKGROUND OF THE INVENTION

The present invention relates to the mounting of a pellet or tablet-like member in order to optimize exposure of the tablet surface to the surrounding air. More particularly, the present invention relates to a mounting arrangement for a rust and corrosion-inhibiting pellet in a fishing tackle box.

Corrosion and rust are major problems associated with the storage of fishing tackle equipment. Moisture in a fishing tackle box will shortly result in rusting and corrosion of hooks, lures, and all metal gear. A product has recently been made available which, although in the form of a solid tablet, serves as a rust and corrosion inhibitor for surrounding items. More specifically, the product is sold by Northern Instrument Company of Lino Lakes, Minn. under the trademark Zerust and continuously releases chemicals into the surrounding air. These released chemicals form a molecular film coating over surrounding items, which coating protects the items from the damaging effects of moisture.

In order to maximize the efficiency of the release of chemicals into an enclosed space it is important that the tablet be mounted so as to expose a maximum of its surface to the air. In other words, the mounting structure itself should contact as little of the tablet as possible while reliably holding the tablet in place. In addition, the mounting structure should permit air to flow freely about the supported tablet in order that the released chemicals may be carried throughout the enclosed space. Further, the mounting structure should securely hold the tablet in place but must also permit easy replacement and removal.

It is therefore an object of the present invention to provide a mounting arrangement for a rust and corrosion inhibiting tablet in a fishing tackle box wherein the tablet is firmly held in place with a maximum of its surface area exposed to surrounding air. It is a further object of the present invention to provide such mounting arrangement with the capability of easy removal and replacement of the tablet.

SUMMARY OF THE INVENTION

In accordance with the present invention, a module for supporting a tablet-like rust and corrosion inhibitor has a slotted front wall and a partially slotted top wall to permit air to freely enter and leave the module interior. Two support vanes project into the module interior from the front wall and a third support vane projects into the interior from the rear wall. The support vanes terminate in lineal edges between which the tablet is wedged so that only the lines of contact are covered from the surrounding air. The tablet is inserted into the module through an open bottom end. A pair of centering vanes extend into the module interior from the module top wall and contact the rim of the tablet during insertion so as to guide the tablet to a centered position in the module.

The module is removable from a snap-fit engagement provided within a tackle box. The snap-fit engagement is formed at the juncture of two walls of the tackle box which meet at a right angle. To this end the module has a rear wall which extends transversely beyond the module side walls to define end flanges which slidably engage respective shoulder surfaces projecting from one of the tackle box walls. A projection from that wall urges the module rear wall forward so that the flanges are forced against the shoulder surfaces in tight slidable engagement. Tiny projections also extend from that same wall of the box to extend over the module and prevent it from being removed from the snap-fit engagement unless the module is first pulled forward to clear the tiny projections and then slid upward until the flanges are disengaged from the shoulder surfaces. A track defined in the other wall of the fishing tackle box receives the edge of the open module end when the module is properly positioned.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings, wherein:

FIG. 1 is a partially cut-away view in perspective of a fishing tackle box showing the module and snap-fit engagement therefor of the present invention inside the box;

FIG. 2 is an exploded detailed view in perspective of the module and snap-fit engagement of FIG. 1;

FIG. 3 is a front view in plan of the module of the present invention;

FIG. 4 is a bottom view in plan of the module of FIG. 3;

FIG. 5 is a view in section taken along lines 5—5 of FIG. 3; and

FIG. 6 is a view in section taken along lines 6—6 of FIG. 4.

DESCRIPTION OF THE PREFERRED EMBODIMENTS

Referring to the drawings in greater detail, a fishing tackle box 10 or any other such container has a side wall 11 and bottom wall 13 which meet one another at a substantially right angle. A module 15, within which a rust and corrosion inhibitor tablet 17 is mounted, can be secured inside the fishing tackle box 10 at the intersection of walls 11 and 13 by means of a snap-fit engagement generally designated by the reference numberal 20.

The module 15 is an integrally-formed molded plastic unit having a front wall 21 with a plurality of longitudinally-extending spaced slots 23 defined therethrough. The front wall curves smoothly into a top wall 25 along which the slots 23 partially extend. Side walls 27 and 29 of the module are closed as is rear wall 30 which extends transversely beyond the sidewalls 27 and 29 to define respective forward-facing flat flanges 31 and 33 on either side of the module. Rear wall 30 is longitudinally shorter than front wall 21 and side wall 27, 29 so that the rear wall does not extend all the way to the module bottom. The bottom of the module is open and is defined at its periphery by the thin downwardly facing lower edge 35 of front wall 21 and similar lower edges of side walls 27 and 29. The lower edges of the side walls do not extend as far as front wall edge 35 which constitutes the lowermost extremity of the module. The upper edge of rear wall 30 is continuous with the module top wall 25 and extends rearward of the longitudinal portion of the rear wall to define a ledge 37. This ledge 37 is the rearward most extremity of the module.

The module interior includes a first support vane 39 extending forwardly from rear wall 30 to terminate in a longitudinally extending thin support edge. Second and third support vanes 40, 41 extend rearwardly from front wall 21 and terminate in respective co-planar longitudinally-extending thin support edges. The support edge of vane 39 resides in a transversely extending plane which is spaced a predetermined distance from the transversely extending plane defined by the support edges of vanes 40, 41. That predetermined distance is equal to the thickness of tablet 17 which can therefore be firmly engaged in the module when it is inserted through the open module bottom between the support edges of vanes 39, 40 and 41. Vane 39 has its support edge positioned substantially on the transverse center line of the module. The support edges of vanes 40 and 41 are transversely spaced by approximately equal transverse distances on either side of vane 39 and such that the spacing between vanes 40 and 41 is considerably less than the diameter of tablet 17.

A pair of centering vanes 43 and 45 are formed integral with rear wall 30 and top wall 25 and include downward facing tablet contact edges which are transversely symmetrically spaced with respect to the support edge of vane 39. The spacing between the contact edges of centering vanes 43, 45 is less than the diameter of tablet 17 but somewhat greater than the spacing between the support edges of vanes 40 and 41. When tablet 17 is inserted through the open bottom of the module, the contact edges of centering vanes 43 and 45 contact the tablet rim and limit the extent of insertion. At the same time, the symmetrical spacing between the centering vanes assures that the fully inserted tablet is transversely centered in the module and thereby centered with respect to support vane 39. In this position the tablet is firmly gripped but only along the lines of the edges of the support vanes 39, 40 and 41. The remainder of the tablet, except for the contact at the edges of the centering vanes, is exposed to air. The slots 23 assure that air can freely enter and leave the module interior.

The snap-fit engagement 20 includes a pair of flange members 51, 53 which are integral with sidewall 11 of the fishing tackle box along the rear edges and with the bottom wall 13 of the box along their bottom edges. Flanges 51 and 53 are transversely spaced by a distance greater than or equal to the largest transverse dimension of rear wall 30 of the module 15. These flanges also include shoulder portions 55, 57 which project transversely toward one another at a distance from box wall 11 which is approximately equal to the spacing between the rearward-most extremity of ledge 37 and the forward-facing surfaces 31, 33 of the flanges formed at the transverse ends of the module rear wall. The rearward facing surfaces of shoulders 55, 57 are adapted to slidably contact respective flange surfaces 31, 33 when the module is properly dropped in the snap-fit engagement 20. A pair of projecting members 59 and 60 extend forwardly of box wall 11 at locations transversely intermediate flanges 51, 53 so as to contact the exposed surface of the module rear wall 30 and thereby urge the module forward in order that surfaces 31, 33 will be in firm contact with respective shoulder portions 55, 57. In this regard, the transverse plane formed by the forward most portions of projections 59 and 60 is spaced from the plane of rearward facing slide surfaces of shoulder portions 55 and 57 by a distance slightly less than or equal to the front to back thickness of rear module wall 30. A pair of forward-projecting nubs 61, 63 are formed integrally with respective projections 59, 60 at locations just above ledge 37 when the module is properly positioned in the snap-fit engagement 20. Nubs 61, 63 engage the module at the top of ledge 37 to prevent inadvertent removal of the module from the engagement. The nubs, in effect, serve to provide the "snap-fit" function of the engagement.

A pair of lip members 65, 67 are formed integrally with box wall 13 and have transverse contours which match the lower edges of respective module side walls 27, 29 and the adjacent portion of the lower edge of front wall 21. Lip members 65, 67 are disposed just forwardly of bottom edge of the module when the module is properly positioned in engagement 20 to serve as a forward stop for the module bottom. A pair of retainer members 69, 70 are formed integrally with bottom box wall 13 and are spaced rearwardly of respective lip members 65, 67 by a distance slightly greater than the thickness of front wall 21 of the module. Lip members 65, 67 and retainer members 69, 70 thus define a track adapted to receive the bottom edge of the module and prevent it from movement along box wall 13. In addition, the lip members serve to prevent a fishing hook or the like catching edge 35 and resulting in the inadvertent removal of the module.

The module 15 is inserted into engagement 20 by lowering the module from above the engagement such that the rearward facing surfaces of shoulders 55, 57 slidably contact forward facing surfaces 31, 33, respectively of the module. As the module is lowered, projections 59, 60 contact the module rear wall 30 and force the surfaces 31, 33 into firm sliding contact with the surfaces of shoulders 55, 57, respectively. When ultimately lowered, the module has its bottom edge retained between forward members 65, 67 and rearward members 69, 70. In addition, ledge 37 slides down past nubs 61, 63 so that the module cannot be moved back up and out of engagement 20 unless it is consciously forced upward to move the ledge upwardly past the nubs.

The module, when positioned in engagement 20, supports tablet 17 in a manner whereby air in the fishing tackle box 10 contacts almost all of the tablet surface. Any movement of air within the box carries the chemicals discharged by the tablet throughout the box to coat the stored fishing tackle items with a rust and corrosion inhibiting film. The module itself is made in one piece by injection molding or other plastic molding processes. In addition, the snap-fit engagement 20 is formed integrally with the box 10. The mounting arrangement for the tablet is therefore simple and inexpensive and yet provides rigid mounting for the tablet while exposing a maximum tablet surface area to surrounding air.

While I have described and illustrated a specific embodiment of my invention, it will be clear that variations from the details of construction which are specifically illustrated and described may be resorted to without departing from the true spirit and scope of the invention as defined in the appended claims.

What I claim is:

1. A structure for firmly supporting a tablet-like member while exposing a maximum of surface area of the tablet-like member to ambient air, said tablet having a predetermined width, a predetermined length and an edge of predetermined thickness, wherein said structure is an integrally-formed plastic unit comprising:

an enclosure having front and rear walls, at least a first of which is provided with a plurality of openings to permit air to freely flow into said enclosure, and an open end for permitting edgewise insertion of said tablet-like member into said enclosure between said front and rear walls;

first and second support members projecting inwardly of said enclosure a first predetermined distance from one of said front and rear walls, said support members terminating in respective first and second substantially parallel longitudinally-extending edges spaced transversely from one another by a distance which is less than said predetermined width; and a third support member projecting inwardly of said enclosure rfrom the other of said front and rear walls and terminating in a third longitudinally-extending edge disposed substantially parallel to said first and second edges and disposed at a transverse location intermediate said first and second edges, said third edge residing in a first plane which is parallel to a second plane defined by said first and second edges and which is spaced from said second plane by a distance substantially equal to said predetermined thickness so that the tablet-like member can be inserted edgewise between the third edge on one side and the first and second edges on its other side and firmly held in said enclosure.

2. The structure according to claim 1 further comprising centering means for transversely centering said tablet-like member with respect to said first and second edges.

3. The structure according to claim 1 wherein said third edge is at least partially co-extensive in a lengthwise sense with said first and second edges.

4. A structure for firmly supporting a tablet-like member while exposing a maximum of surface area of the tablet-like member to ambient air, said structure comprising:

an enclosure having front and rear walls, at least a first of which is provided with a plurality of opnings to permit air to freely flow into said enclosure;

first and second support members projecting inwardly of said enclosure a first predetermined distance from one of said front and rear walls, said support members terminating in respective first and second substantially parallel longitudinally-extending edges spaced transversely from one another by a distance which is less than the width of said tablet-like member;

a third support member projecting inwardly of said enclosure from the other of said front and rear walls and terminating in a third longitudinally-extending edge disposed substantially parallel to said first and second edges and disposed at a transverse location intermediate said first and second edges, said third edge residing in a first plane which is parallel to a second plane defined by said first and second edges and which is spaced from said second plane by a distance substantially equal to the thickness of said tablet-like member so that the tablet-like member can be inserted between the third edge on one side and the first and second edges on its other side and firmly held in said enclosure; and centering means for transversely centring said tablet-like member with respect to said first and second edges;

wherein said tablet-like member is a round disc with a cylindrical edge, wherein said third edge is transversely positioned substantially mid-way between said first and second edges, wherein said enclosure is open at one end to permit edgewise insertion of said tablet-like member into said enclosure in a direction parallel to said first and second planes, and wherein said centering means comprises first and second end members terminating in respective fourth and fifth edges facing said open one end of said enclosure and transversely spaced from one another by less than the width of said tablet-like member, said fourth and fifth edges being at least partially disposed between said first and second planes so as to contact the edge of the tablet-like member at two locations and thereby limit further edgewise insertion of the tablet-like member into the enclosure.

5. A structure for firmly supporting a tablet-like member while exposing a maximum of surface area of the tablet-like member to ambient air, said structure comprising:

an enclosure having front and rear walls, at least a first of which is provided with a plurality of openings to permit air to freely flow into said enclosure;

first and second support members projecting inwardly of said enclosure a first predetermined distance from one of said front and rear walls, said support members terminating in respective first and second substantially parallel longitudinally-extending edges spaced transversely from one another by a distance which is less than the width of said tablet-like member; and a third support member projecting inwardly of said enclosure from the other of said front and rear walls and terminating in a third longitudinally-extending edge disposed substantially parallel to said first and second edges and disposed at a transverse location intermediate said first and second edges, said third edge residing in a first plane which is parallel to a second plane defined by said first and second edges and which is spaced from said second plane by a distance substantially equal to the thickness of said tablet-like member so that the tablet-like member can be inserted between the third edge on one side and the first and second edges on its other side and firmly held in said enclosure;

wherein said front wall is provided with said plurality of openings in the form of slots which extend longitudinally parallel to said first, second and third edges, wherein said enclosure has an open bottom end defined by a bottom extremity of said front wall to permit insertion of said tablet-like member into said enclosure in a direction parallel to said first and second planes, wherein said rear wall extends transversely beyond the transverse extremities of said front wall, wherein said front and rear walls are joined by sidewalls which terminate at locations on said rear wall which are transversely inward of the rear wall ends to define longitudinally-extending forward-facing shoulders on said rear wall outside said enclosure, and wherein the top end of said enclosure is at least partially closed and includes a projecting portion extending rearwardly of said rear wall.

6. The structure according to claim 5 further comprising a mounting support for said structure including first and second walls joining one another at right angles, first and second flange members projecting forwardly of said first wall and upwardly of said second wall and transversely spaced by distance no less than the transverse dimension of said rear wall, the forwardmost extremities of said flange members terminating in rearward-facing shoulders projecting transversely toward one another to provide mating slide surfaces for the respective forward-facing shoulders defined at the ends of said rear wall when said structure is inserted from above with said rear wall facing said first wall and said open end facing said second wall.

7. The structure according to claim 6 further comprising at least one projection extending forwardly from said first wall to reside in a third plane which is parallel to a fourth plane defined by said rearward facing shoulders and spaced from said fourth plane by a distance substantially equal to the thickness of said rear wall to firmly force said forward facing shoulders against said rearward facing shoulders.

8. The structure according to claim 7 further comprising a track defined in said second wall and contoured to receive and positionally stabilize the bottom edge of said front wall when said structure is fully inserted in said mounting support.

9. The structure according to claim 8 further comprising means projecting from said first wall at a position to overhang the projecting portion of said top wall when said structure is fully inserted into said mounting support to provide a snap-fit engagement of said structure in said mounting support.

10. The structure according to claim 9 wherein said slots in said front wall extend partially along said top wall.

11. A structure for firmly supporting a tablet-like member having a predetermined length, a predetermined width and a predetermined thickness, while exposing a maximum surface area of said tablet-like member to ambient air, said structure comprising:
   an enclosure having front and rear walls, at least a first of which is provided with a plurality of openings to permit air to freely flow into said enclosure;
   first and second support members projecting inwardly of said enclosure a first predetermined distance from one of said front and rear walls, said support members terminating in respective first and second substantially parallel longitudinally-extending edges which are spaced transversely from one another by a distance which is less than said predetermined width; and
   a third support member projecting inwardly of said enclosure from the other of said front and rear walls and terminating in a third longitudinally-extending edge disposed substantially parallel to said first and second edges and disposed at a tranverse location intermediate said first and second edges, said third edge residing in a first plane which is parallel to a second plane defined by said first and second edges and which is spaced from said second plane by a distance substantially equal to said predetermined thickness so that the tablet-like member can be inserted between the third edge on one side and the first and second edges on its other side and firmly held in said enclosure;
   wherein said third edge is at lest partially co-extensive in a lengthwise sense with said first and second edges to preclude application of a net turning moment to said tablet-like member by said first, second and third edges about a transversely-extending axis.

* * * * *